(12) United States Patent
Kojima et al.

(10) Patent No.: US 9,610,090 B2
(45) Date of Patent: Apr. 4, 2017

(54) LIQUID INJECTION DEVICE AND MEDICAL DEVICE

(71) Applicant: SEIKO EPSON CORPORATION, Tokyo (JP)

(72) Inventors: Hideki Kojima, Matsumoto (JP); Hirokazu Sekino, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 226 days.

(21) Appl. No.: 14/491,159

(22) Filed: Sep. 19, 2014

(65) Prior Publication Data

US 2015/0080923 A1 Mar. 19, 2015

(30) Foreign Application Priority Data

Sep. 19, 2013 (JP) .................. 2013-193732

(51) Int. Cl.
*A61B 17/3203* (2006.01)
*A61B 17/00* (2006.01)

(52) U.S. Cl.
CPC ...... *A61B 17/3203* (2013.01); *A61B 2017/00154* (2013.01); *A61B 2017/00455* (2013.01); *A61B 2017/32032* (2013.01); *Y10T 137/8593* (2015.04)

(58) Field of Classification Search
CPC .......... A61B 17/3203; A61B 17/32037; A61B 2017/00154; A61B 2017/32032; A61B 2017/32035
See application file for complete search history.

(56) References Cited

U.S. PATENT DOCUMENTS

| | | | |
|---|---|---|---|
| 7,901,374 B2 | 3/2011 | Seto et al. | |
| 8,919,664 B2 | 12/2014 | Seto et al. | |
| 2009/0270799 A1 | 10/2009 | Seto et al. | |
| 2010/0010524 A1* | 1/2010 | Barrington | A61B 17/3203 606/167 |
| 2011/0215170 A1 | 9/2011 | Kojima | |
| 2012/0089164 A1 | 4/2012 | Kojima et al. | |

FOREIGN PATENT DOCUMENTS

| | | |
|---|---|---|
| JP | 2000-145649 A | 5/2000 |
| JP | 2008-082202 A | 4/2008 |
| JP | 2011-177407 A | 9/2011 |
| JP | 2011-193949 A | 10/2011 |
| JP | 2012-082739 A | 4/2012 |
| JP | 2012-144989 A | 8/2012 |
| JP | 2012-223266 A | 11/2012 |
| JP | 2013-056016 A | 3/2013 |

OTHER PUBLICATIONS

Extended European Search Report dated Jan. 7, 2015 as received in Application No. 14185327.5.

* cited by examiner

*Primary Examiner* — Todd J Scherbel
(74) *Attorney, Agent, or Firm* — Maschoff Brennan

(57) ABSTRACT

A liquid injection device that injects a liquid includes a liquid chamber, a first channel connected to the liquid chamber and feeding a liquid to the liquid chamber, a second channel connected to the liquid chamber, to which the liquid is fed from the liquid chamber, and an injection tube that communicates with the second channel and injects the liquid, and the second channel has a curved shape.

16 Claims, 6 Drawing Sheets

LIQUID INJECTION DEVICE AND MEDICAL DEVICE

This patent application claims the benefit of Japanese Patent Application No. 2013-193732, filed on Sep. 19, 2013. The content of the aforementioned application is hereby incorporated by reference in its entirety.

BACKGROUND

1. Technical Field

The present invention relates to a liquid injection device that injects a liquid and a medical device using the liquid injection device.

2. Related Art

A liquid injection device that suctions and removes an excised piece excised by a liquid injected from an injection channel via a suction channel is known (e.g., Patent Document 1 (JP-A-2008-82202)).

The liquid injection device of Patent Document 1 has an advantageous structure in which a liquid fed from an entrance channel is pulsed by an actuator to flow out from an exit channel and the pulsed liquid is injected from an injection port.

While the advantage of the structure is taken, further downsizing (thinning) of the structure has been pursued. Furthermore, in the liquid injection device, lower cost, resource saving, facilitation of manufacture, improvement in usability, etc. have been desired.

SUMMARY

An advantage of some aspects of the invention is to solve at least a part of the problems described above, and the invention can be implemented as the following forms.

(1) An aspect of the invention provides a liquid injection device that injects a liquid. The liquid injection device includes a liquid chamber, a first channel connected to the liquid chamber and feeding a liquid to the liquid chamber, a second channel connected to the liquid chamber, to which the liquid is fed from the liquid chamber, and an injection tube that communicates with the second channel and injects the liquid, wherein the second channel has a curved shape. According to the liquid injection device of the embodiment, the second channel has the curved shape, and thus, the total width of the liquid chamber and the second channel may be made smaller.

(2) In the liquid injection device of the aspect of the invention described above, the first channel and the second channel may be connected to a first surface of the liquid chamber, and the second channel may be connected to a position different from a face center in the first surface. According to the liquid injection device of this configuration, the second channel may be connected to the first surface with separation ensured from the first channel.

(3) In the liquid injection device of the aspect of the invention described above, the first channel and the second channel may be connected to a first surface of the liquid chamber, and the first channel may be connected to a position different from a face center in the first surface. According to the liquid injection device of this configuration, the first channel may be connected to the first surface with separation ensured from the second channel.

(4) In the liquid injection device of the aspect of the invention described above, a curve angle X of the curved shape in the second channel may be $90° \leq X \leq 270°$. According to the liquid injection device of this configuration, the curve angle X is $90° \leq X \leq 270°$ and, compared to the case where $X \leq 90°$ or $X \geq 270°$, the total width of the liquid chamber and the second channel may be made smaller.

(5) In the liquid injection device of the aspect of the invention described above, the curve angle X may be $180° \pm 5°$. According to the liquid injection device of this configuration, the total width of the liquid chamber and the second channel may be made even smaller.

(6) In the liquid injection device of the aspect of the invention described above, a section area of the second channel may be five times or more larger than a section area of the first channel. According to the liquid injection device of this configuration, air bubbles within the liquid chamber may be easily ejected through the second channel.

(7) In the liquid injection device of the aspect of the invention described above, a vertical orientation specification part that specifies a vertical orientation of a container is provided, and the second channel may be connected to an upper position of the first surface than the first channel in the vertical orientation specified by the vertical orientation specification part. According to the liquid injection device of this configuration, the second channel is connected above the first channel, and thereby, air bubbles within the liquid chamber may be easily ejected through the second channel.

(8) In the liquid injection device of the aspect of the invention described above, the second channel may be formed by a metal member. According to the liquid injection device of the aspect of the invention described above, in the part in which the second channel is curved, reduction of the inner diameter may be suppressed.

(9) Another aspect of the invention provides a medical device employing the liquid injection device of the aspect of the invention described above. According to the medical device of this configuration, the liquid injection device having the smaller total width of the liquid chamber and the second channel may be used.

Not all of the plurality of components of the above described respective embodiments of the invention are essential. In order to solve part or all of the above described problems or achieve part or all of the above described advantages described in the specification, changes, deletion, replacement by other new components, partial deletion of the limitations may be appropriately made to part of the components of the plurality of components. Further, in order to solve part or all of the above described problems or achieve part or all of the above described advantages described in the specification, part or all of the technological features contained in the above described one embodiment of the invention may be combined with part or all of the technological features contained in the above described other embodiments of the invention, and thereby, one independent embodiment of the invention may be formed.

For example, one embodiment of the invention may be implemented as a device including one or more elements of the four elements of the liquid chamber, the first channel, the second channel and the injection tube. That is, the device may have the liquid chamber or not. Further, the device may have the first channel or not. Furthermore, the device may have the second channel or not. For example, the first channel may be formed as a first channel connected to the liquid chamber and feeding a liquid to the liquid chamber. The second channel may be formed as a second channel connected to the liquid chamber, to which the liquid is fed from the liquid chamber. The injection tube may be formed as an injection tube communicating with the second channel and injecting the liquid. Such a device may be implemented as the liquid injection device, however, may be implemented as other devices than the liquid injection device. According to the embodiments, at least one of various issues of downsizing, lower cost, resource saving, facilitation of manufacture, improvement in usability of the device, etc. may be resolved. Part or all of the technological features of the above described respective embodiments of the liquid injection device may be applied to the device.

The invention may be implemented in other various forms than the devices. For example, the invention may be implemented in forms of a method of injecting a liquid, a method of manufacturing a liquid injection device, etc.

BRIEF DESCRIPTION OF THE DRAWINGS

The invention will be described with reference to the accompanying drawings, wherein like numbers reference like elements.

DESCRIPTION OF EXEMPLARY EMBODIMENTS

A. First Embodiment

Figure 1:
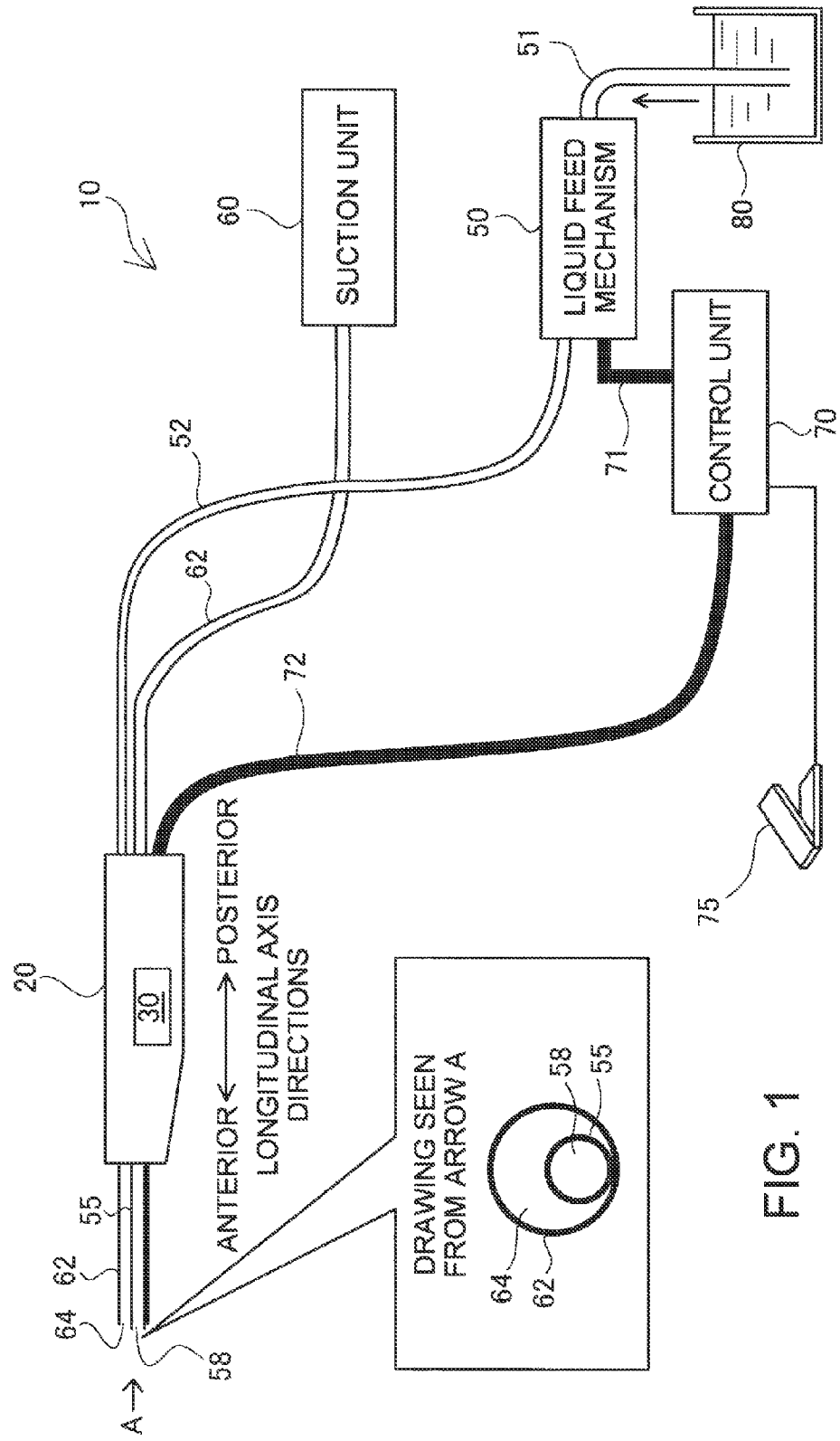
FIG. 1 is an explanatory diagram for explanation of a configuration of a liquid injection device.

FIG. 1 is an explanatory diagram for explanation of a configuration of a liquid injection device 10 as the first embodiment of the invention. The liquid injection device 10 of the embodiment is a medical device used as a scalpel for incision or excision of an affected part by injecting a liquid to the affected part.

The liquid injection device 10 includes a hand piece 20 as a container, a liquid feed mechanism 50, a suction unit 60, and a control unit 70. A liquid is fed from a liquid container 80 to the liquid injection device 10. The liquid feed mechanism 50 and the liquid container 80 are connected by a connecting tube 51. The liquid feed mechanism 50 and the hand piece 20 are connected by a liquid feed channel 52. In the embodiment, the connecting tube 51 and the liquid feed channel 52 are formed using resin.

The liquid container 80 contains saline as a liquid. The liquid feed mechanism 50 feeds the liquid suctioned from the liquid container 80 via the connecting tube 51 to the hand piece 20 via the liquid feed channel 52. The saline is employed as the liquid in the embodiment, however, not limited to that. Various liquids including sterile water and pure water may be employed.

The hand piece 20 is a tool grasped and operated by a user of the liquid injection device 10. The hand piece 20 includes an actuator 30, an injection tube 55, an injection port 58, and a suction force adjustment mechanism 65. In the embodiment, the directions along the injection tube 55 of the hand piece 20 are referred to as axial directions. Of the axial directions, the direction toward the injection tube 55 is an anterior direction. Pulsation at a predetermined frequency is provided by the actuator 30 to the liquid fed from the liquid feed mechanism 50 via the liquid feed channel 52 to the hand piece 20, and the liquid is fed to the injection tube 55. The liquid fed to the injection tube 55 is injected as a pulsed liquid from the injection port 58. The user applies the pulsed liquid injected from the injection port 58 to an affected part of a patient, and thereby, incises or excises the affected part. In the embodiment, the injection tube 55 is formed using stainless. Note that the injection tube 55 may be formed using a material having predetermined or more rigidity such as other metals including brass or reinforced plastic. The suction force adjustment mechanism 65 is a mechanism for the user to adjust the degree of suction by the suction unit 60. In the embodiment, the amount of suction per unit time is employed as an index indicating the degree of suction.

The control unit 70 transmits a drive signal to the actuator 30 via a signal cable 72 and controls the liquid feed mechanism 50 via a control cable 71, and thereby, controls a flow rate of the liquid fed to the actuator 30. A foot switch 75 operated by the user beneath the foot is connected to the control unit 70. When the user turns on the foot switch 75, the control unit 70 controls the liquid feed mechanism 50 to allow the actuator 30 to feed the liquid and transmit the drive signal to the actuator 30, and provides pulsation to the liquid fed to the actuator 30 and injects the pulsed liquid from the injection port 58. Note that the pulsed injection of the liquid means injection of the liquid with variations of the flow rate or flow velocity of the injected liquid. The form of the pulsed injection of the liquid includes intermittent injection of repeated injection of the liquid and halt, however, is not necessarily the intermittent injection as long as the flow rate or flow velocity of the injected liquid may vary.

The suction unit 60 suctions the liquid around the injection port 58, an excised piece (hereinafter, also referred to as "suctioned piece"), or the like. The suction unit 60 and the hand piece 20 are connected by a suction channel 62. The suction channel 62 is extended to the vicinity of the end of the injection tube 55 through the hand piece 20. The injection tube 55 is inserted into the suction channel 62. As shown in a drawing seen from an arrow A of FIG. 1, a channel in which the liquid suctioned from a suction port 64 as the end of the suction channel 62 flows (hereinafter, also referred to as "clearance channel") is formed between the outer wall of the injection tube 55 and the inner wall of the suction channel 62. The liquid flowing from the suction port 64 into the clearance channel is suctioned by the suction unit 60 via the suction channel 62. The amount of suction per unit time suctioned from the suction port 64 is adjustable by the user operating the suction force adjustment mechanism 65.

Figure 2:
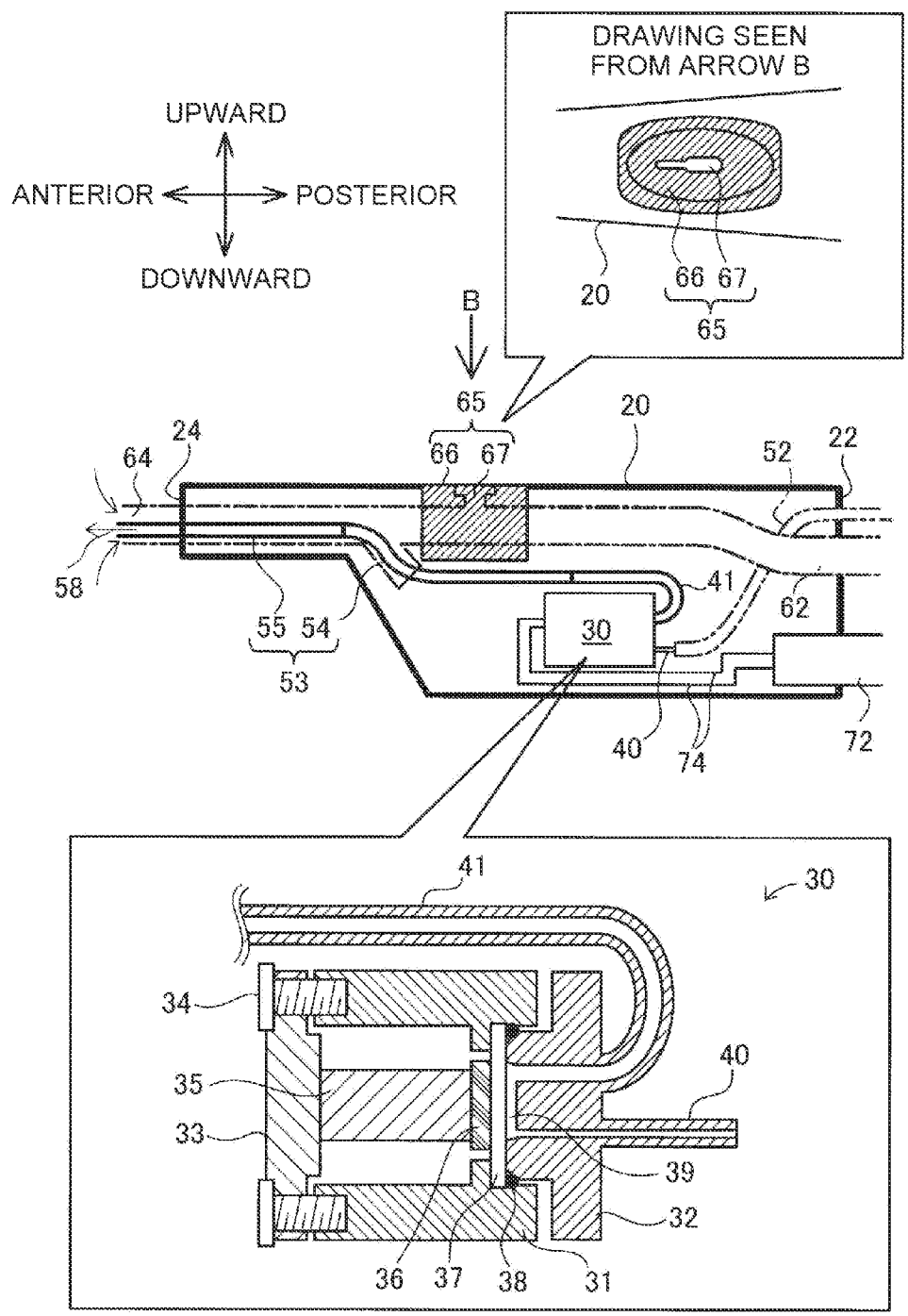
FIG. 2 is an explanatory diagram for explanation of an internal structure of a hand piece.

FIG. 2 is an explanatory diagram for explanation of an internal structure of the hand piece 20. First, the structure of the actuator 30 is explained. As shown in the lower part of the drawing, the actuator 30 includes a first case 31, a second case 32, a third case 33, a bolt 34, a piezoelectric element 35, a reinforcing plate 36, a diaphragm 37, a packing 38, a first channel 40, and a second channel 41. The first case 31 and the second case 32 are opposed and bonded. The first case 31 is a tubular member. One end of the first case 31 is sealed by fixation of the third case 33 with the bolt 34. The piezoelectric element 35 is provided in a space formed within the first case 31.

The piezoelectric element 35 is a multilayer piezoelectric element. One end of the piezoelectric element 35 is fixed to the diaphragm 37 via the reinforcing plate 36. The other end of the piezoelectric element 35 is fixed to the third case 33. The diaphragm 37 is formed using a metal thin film and its peripheral edge is fixed to the first case 31. A liquid chamber 39 is formed between the diaphragm 37 and the second case 32. The liquid chamber 39 has a volume changed by driving of the piezoelectric element 35.

The second case 32 has two through holes. To the respective through holes, the first channel 40 into which the liquid flows and the second channel 41 from which the liquid flows out are connected. The first channel 40 and the second channel 41 are connected to the posterior end surface of the actuator 30, i.e., the end surface of the second case 32 and extended. The extension forms of the first channel 40 and the second channel 41 from the second case 32 will be explained later in detail.

The liquid feed channel 52 is connected to the first channel 40. The injection tube 55 is connected to the second channel 41 via a connecting tube 54. The channel including the two pipe lines of the connecting tube 54 and the injection tube 55 is also referred to as "injection channel 53". The liquid fed from the liquid feed mechanism 50 is fed to the liquid chamber 39 via the liquid feed channel 52 and the first channel 40. When the piezoelectric element 35 vibrates at a predetermined frequency, the volume of the liquid chamber 39 is changed via the diaphragm 37 and the contained liquid is pressurized. The pressurized liquid passes through the second channel 41, the connecting tube 54, and the injection tube 55 and is ejected from the injection port 58.

The suction channel 62 communicates from a posterior end part 22 to an anterior end part 24 of the hand piece 20. Within the hand piece 20, the injection channel 53 is inserted into the suction channel 62. The suction channel 62 is drawn from the anterior end part 24 of the hand piece 20 with the injection tube 55.

Inside the hand piece 20, the injection channel 53 and the suction channel 62 are separated. In the separation part of the two channels, the injection channel 53 is curved with respect to the suction channel 62 and separated. In the separation part, it is preferable that the injection channel 53 is gently curved and the curvature is smaller. In the separation part, the suction channel 62 is provided in a nearly linear shape. Note that the form in which the suction channel 62 is provided in the nearly linear shape is employed in the separation part in the embodiment, however, the suction channel 62 may be provided in a curved shape having the smaller curvature than the curvature of the injection channel in the separation part.

Of the pipe lines forming the injection channel 53, the connecting tube 54 is provided nearly in parallel to the axial direction of the hand piece 20 having a columnar shape posterior to separation from the suction channel 62, and connected to the second channel 41. Further, in the embodiment, the connecting tube 54 posterior to separation is provided nearly in parallel to the suction channel 62.

The suction force when the suction channel 62 suctions the liquid or the like from the suction port 64 is adjustable by the suction unit 60, and adjustable by the user operating an operation part 66 of the suction force adjustment mechanism 65 of the hand piece 20.

The suction force adjustment mechanism 65 includes the operation part 66 and a suction adjustment hole 67. The suction force adjustment mechanism 65 is a member formed using resin. Inside the suction force adjustment mechanism 65, a channel constituting apart of the suction channel 62 is formed. Actually, the suction channel 62 is connected to both ends of the channel formed in the suction force adjustment mechanism 65. The operation part 66 is a part of the suction force adjustment mechanism 65 exposed to the outside of the hand piece 20 and operated by the user with a finger.

The suction adjustment hole 67 communicates with the suction channel 62 and the operation part 66. As shown in the drawing seen from an arrow B of FIG. 2, an opening portion of the suction adjustment hole 67 is formed in the operation part 66. When grasping the hand piece 20, the user opens and closes the suction adjustment hole 67 with the finger. The suction force adjustment mechanism 65 adjusts an amount of air flowing from the outside into the suction channel 62 via the suction adjustment hole 67 according to the size of the surface area of the suction adjustment hole 67 closed by the user, and adjusts the pressure within the suction channel 62 (hereinafter, also referred to as "suction pressure"). That is, the suction force adjustment mechanism 65 adjusts the amount of suction per unit time.

The suction adjustment hole 67 is provided on the suction channel 62 posterior to the separation of the injection tube 55. In other words, the suction adjustment hole 67 is provided on the suction channel 62 at the posterior end side of the separation part of the injection tube 55 and the suction channel 62.

The suction force adjustment mechanism 65 preferably exhibits its function when directed upward with respect to the gravitational force because the suctioned piece is extremely harder to exit from the suction adjustment hole 67 to the outside. When grasping the hand piece 20, the user directs the suction force adjustment mechanism 65 upward and closes the suction adjustment hole 67 of the operation part 66 downward with the finger, and thereby, adjusts the amount of suction per unit time of the suction unit 60. Incidentally, the positions of the respective configurations of the liquid injection device 10 are determined so that the function of the suction force adjustment mechanism 65 and the operability of the user may be preferable when the suction force adjustment mechanism 65 is grasped upward, however, the suction force adjustment mechanism 65 does not necessarily force the user to use the hand piece 20 directed upward. As below, in the hand piece 20, the direction in which the suction force adjustment mechanism 65 is provided is defined as upward.

The signal cable 72 is inserted from the posterior end part 22 of the hand piece 20. Two electrode wires 74 of positive and negative inserted into the signal cable 72 are connected to the piezoelectric element 35 within the actuator 30. The drive signal transmitted from the control unit 70 is transmitted to the piezoelectric element 35 via the electrode lines 74 within the signal cable 72. The piezoelectric element 35 expands and contracts according to the drive signal.

Figure 3:
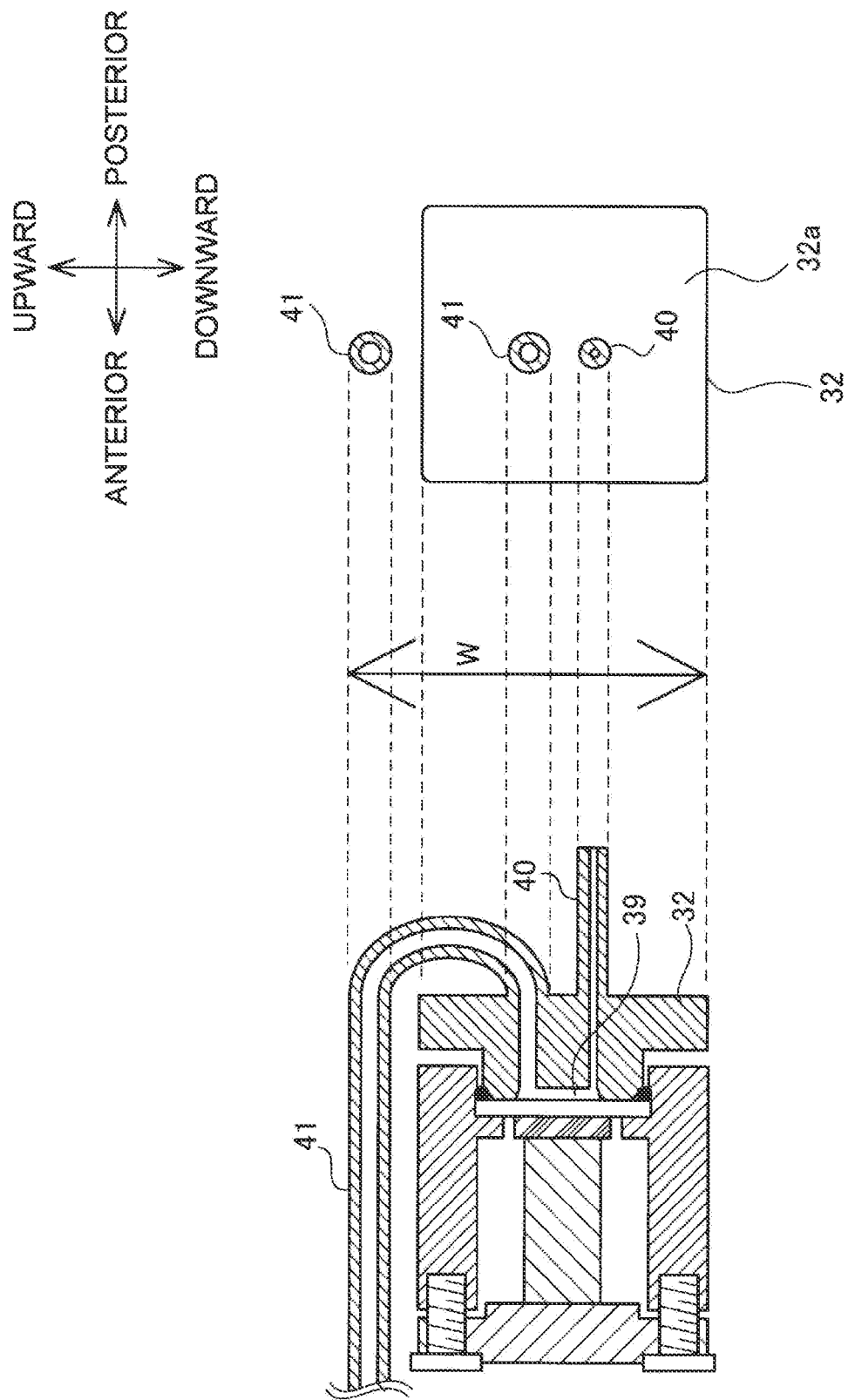
FIG. 3 is an explanatory diagram for explanation of extension forms of a first channel and a second channel.

Next, the extension forms of the first channel 40 and the second channel 41 are explained. FIG. 3 is an explanatory diagram for explanation of the extension forms of the first channel 40 and the second channel 41 from the second case 32. As shown in FIG. 3, the first channel 40 is extended from the second case 32 toward the posterior in the axial direction of the hand piece 20. The second channel 41 is extended from the second case 32, bent in a curved shape, and extended toward the anterior end part 24 of the hand piece 20 (in the anterior direction of FIG. 3). In the embodiment, particularly, the second channel 41 is bent in a U-shape.

In the embodiment, the first channel 40 and the second channel 41 are stainless pipes and connected to the second case 32 by welding. For the first channel 40 and the second channel 41, not limited to stainless, but pipes of other metals such as brass and aluminum may be employed.

As seen from the sectional view along C-C of the actuator 30, the positions where the first channel 40 and the second channel 41 are connected to the second case 32 are positions deviated from the face center of the posterior end surface of the second case 32 (hereinafter, also referred to as "posterior end surface 32a"). That is, the first channel 40 and the second channel 41 are connected to the positions deviated from the face center of the posterior end surface 32a having a nearly rectangular shape. Note that, in the embodiment, the posterior end surface 32a has the nearly rectangular shape, however, as the shape of the posterior end surface 32a, various shapes such as a circular shape, a triangular shape, other polygonal shapes may be employed. For example, in the case of the triangular shape, the first channel 40 and the second channel 41 may be connected to the positions out of the center of gravity of the posterior end surface 32a having the triangular shape. As the face center of the posterior end surface 32a, a singular point of the figure such as the center, the center of gravity, or the like of the posterior end surface 32a may be employed.

When the direction in which the suction force adjustment mechanism 65 is provided in the hand piece 20 is upward, the second channel 41 is connected above the face center of the posterior end surface 32a of the second case 32 and extended. The first channel 40 is connected below the center of the posterior end surface 32a of the second case 32 and extended.

When the first channel 40 and the second channel 41 are provided as described above, the liquid entering the liquid chamber 39 from the first channel 40 flows upward and flows out from the second channel 41. If air bubbles intervene in the liquid chamber 39, the air bubbles move upward due to buoyancy and flow out from the second channel 41.

The channel section area of the second channel 41 is e.g., five times larger than the channel section area of the first channel 40. According to the arrangement of the second channel 41 and the first channel 40 and the difference in channel section area between the channels, when the volume of the liquid chamber 39 varies, the backward flow of the liquid into the first channel 40 is suppressed and ejection of the air bubbles from the liquid chamber 39 to the first channel 40 is promoted. Note that the channel section areas of the second channel 41 and the first channel 40 are not limited to constant, but the channel section areas of the respective channels may be distorted. In this case, it is only necessary that the channel section area of at least part of the second channel 41 is e.g., five times larger than the channel section area of at least part of the first channel 40.

As described above, the second channel 41 has the curved shape (particularly, the U-shape in the embodiment) and is connected to the posterior end surface 32a, and thus, the total width of the actuator 30 and the second channel 41 as seen from the axial direction (front surface of the section along C-C) of the hand piece 20 (the width W in FIG. 3) may be reduced. As a result, the hand piece 20 housing the actuator 30 and the second channel 41 may be reduced. Note that the curved shape in the embodiment corresponds to coupling at an angle (hereinafter, also referred to as "curve angle X") of $90° \leq X \leq 270°$ of the connecting part of the second channel 41 and the connecting tube 54 and the connecting part of the second channel 41 and the actuator 30 (liquid chamber 39) between the connecting part of the second channel 41 and the connecting tube 54 and the connecting part of the second channel 41 and the actuator 30 (liquid chamber 39). Further, the more desirable curve angle X is $X=180°\pm5°$. The curve angle X is employed, and thereby, downsizing of the hand piece 20 may be realized.

The first channel 40 is connected below the face center of the posterior end surface 32a and the second channel 41 is connected above the face center of the posterior end surface 32a and the channels are respectively extended, and thereby, the air bubbles entering the liquid chamber 39 with the liquid flowing from the first channel 40, the air bubbles generated in the liquid chamber 39, etc. move upward due to buoyancy and easily flow out from the second channel 41. Therefore, the pressure applied to the liquid of the liquid chamber 39 by the piezoelectric element 35 is harder to be buffered by the air and the air bubbles mixed into the actuator 30, and the sufficient pulsed flow may be generated by the piezoelectric element 35.

Further, the channel section area of the second channel 41 is e.g., five times larger than the channel section area of the first channel 40, and thus, when the volume of the liquid chamber 39 varies, the backward flow of the liquid into the first channel 40 is suppressed. Further, the ejection of the air bubbles from the liquid chamber 39 to the first channel 40 is promoted.

The first channel 40 and the second channel 41 are connected to the positions deviated from the face center of the posterior end surface 32a and extended, and thus, the channels may be connected to the posterior end surface 32a with the sufficient distance between each other.

The first channel 40 is formed in the form connected to the posterior end surface 32a, and thus, compared to the case where the pipes are connected to the other side surface of the second case 32 and apart of the second case 32 is shaped to form the first channel 40 (e.g., Patent Document 1), the structure of the first channel 40 may be made simpler and the formation of the first channel 40 may be made easier. Further, the first channel 40 in the embodiment may secure the sufficient flow velocity (flow rate) because there is no elbow that may cause the channel resistance.

The second channel 41 is the metal (stainless in the embodiment) pipe, and thus, when the channel is bent in the U-shape, the inner diameter of the pipe is harder to be distorted and the sufficient channel section area may be secured.

As the correspondences between the embodiment and the appended claims, the posterior end surface 32a corresponds to a first surface described in the appended claims. The suction force adjustment mechanism 65 corresponds to a vertical orientation specification part described in the appended claims.

A. Modified Examples

The invention is not limited to the above described embodiment, but may be embodied in various forms without departing from the scope thereof. For example, the following modified examples may be made.

(B1) Modified Example 1

Figure 4:
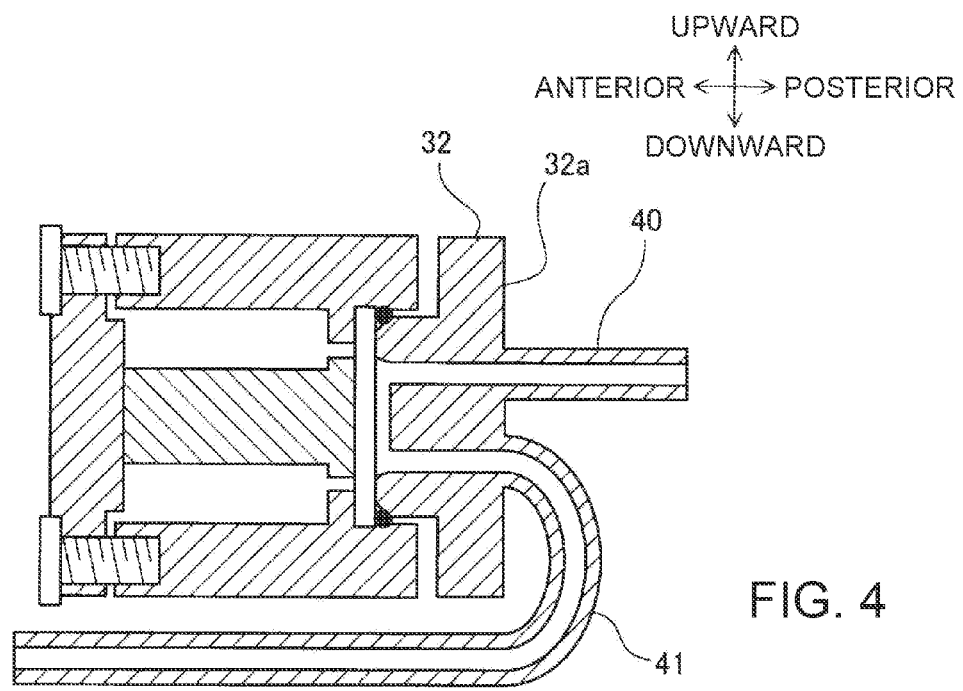
FIG. 4 is an explanatory diagram showing Modified Example 1.

In the embodiment, the extension forms of the first channel 40 and the second channel 41 from the posterior end surface 32a are not limited to the forms shown in FIG. 2, but other extension forms may be employed. As shown in FIG. 4, the first channel 40 may be extended from above the face center of the posterior end surface 32a and the second channel 41 may be extended from below the face center of the posterior end surface 32a, respectively. In the extension forms in FIG. 4, the second channel 41 is extended from below the face center of the posterior end surface 32a and bent downward in a U-shape. According to the configuration, the same advantages as those of the embodiment may be obtained.

Further, in the embodiment, the forms in which both the first channel 40 and the second channel 41 are connected to the positions deviated from the face center of the posterior end surface 32a and extended is employed, however, a form in which one of the first channel 40 and the second channel 41 is extended from the face center of the posterior end surface 32a may be employed.

(B2) Modified Example 2

Figure 5:
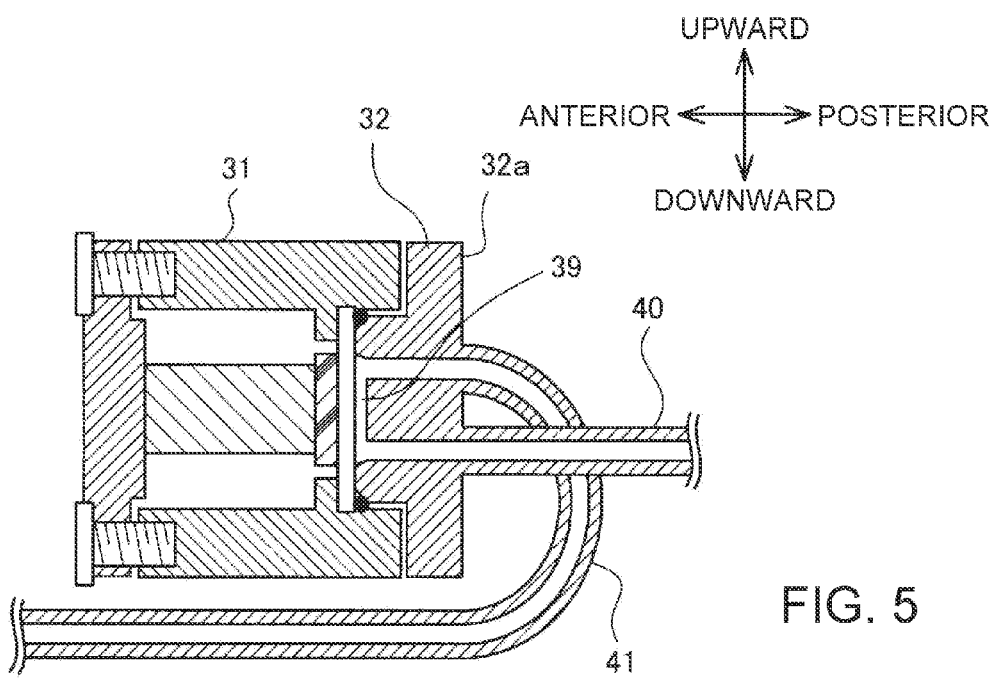
FIG. 5 is an explanatory diagram showing Modified Example 2.

Extension forms in which the first channel 40 and the second channel 41 are crossed may be employed. FIG. 5 is an explanatory diagram showing an example of the extension forms of the first channel 40 and the second channel 41. In the extension forms of FIG. 5, the first channel 40 and the second channel 41 are connected to the positions deviated from the face center of the posterior end surface 32a and extended, and the channels may be connected to the posterior end surface 32a with a sufficient distance between each other. The second channel 41 is connected above the face center of the posterior end surface 32a of the second case 32 and extended, curved downward in a U-shape, crossed with the first channel 40, and extended toward the anterior in the axial direction, and thereby, the curvature of the pipe line in the U-shape may be reduced.

Further, the second channel 41 is connected above the face center of the posterior end surface 32a of the second case 32 and extended. The first channel 40 is connected below the center of the posterior end surface 32a of the second case 32 and extended. Therefore, the liquid entering the liquid chamber 39 from the first channel 40 flows upward and flows out from the second channel 41. If air bubbles intervene in the liquid chamber 39, the air bubbles move upward due to buoyancy and flow out from the second channel 41.

(B3) Modified Example 3

Figure 6:
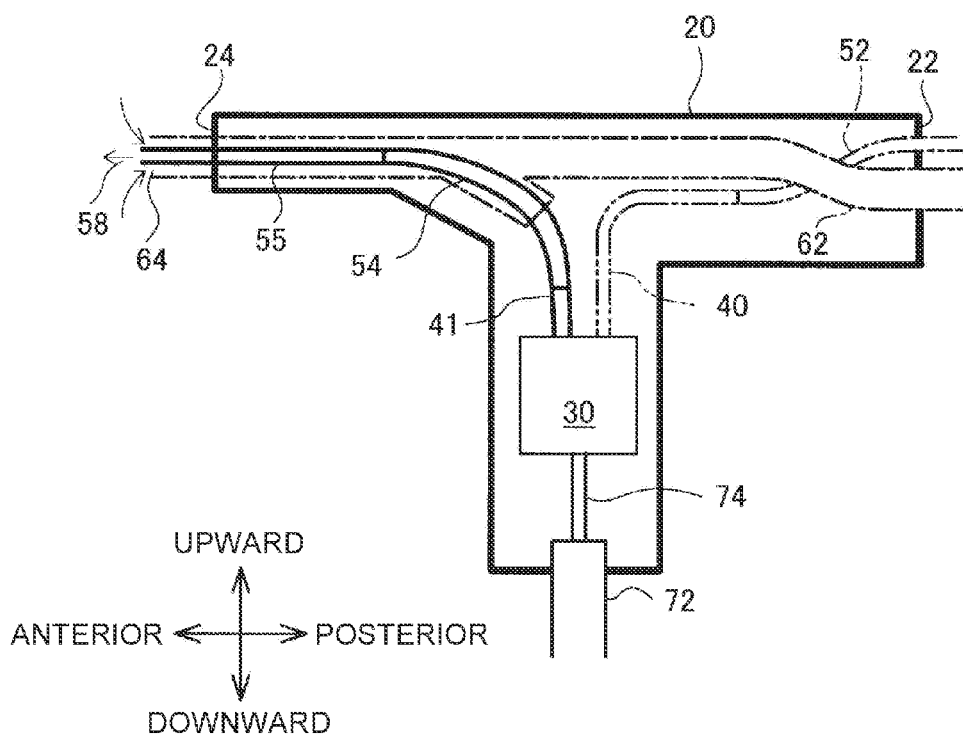
FIG. 6 is an explanatory diagram showing Modified Example 3.

Both the first channel 40 and the second channel 41 may have curved shapes. FIG. 6 is an explanatory diagram showing forms in which the first channel 40 and the second channel 41 have curved shapes. The first channel 40 is extended upward from the upper end surface of the actuator 30, curved, and extended in the posterior direction. The second channel 41 is extended upward from the upper end surface of the actuator 30, curved, and extended in the anterior direction. According to the configuration, the same advantages as those of the embodiment may be obtained.

(B4) Modified Example 4

In the embodiment, the liquid injection device 10 includes the suction force adjustment mechanism 65, however, the suction force adjustment mechanism 65 may not be provided. According to the configuration, the same advantages as those of the embodiment may be obtained.

(B5) Modified Example 5

Figure 7:
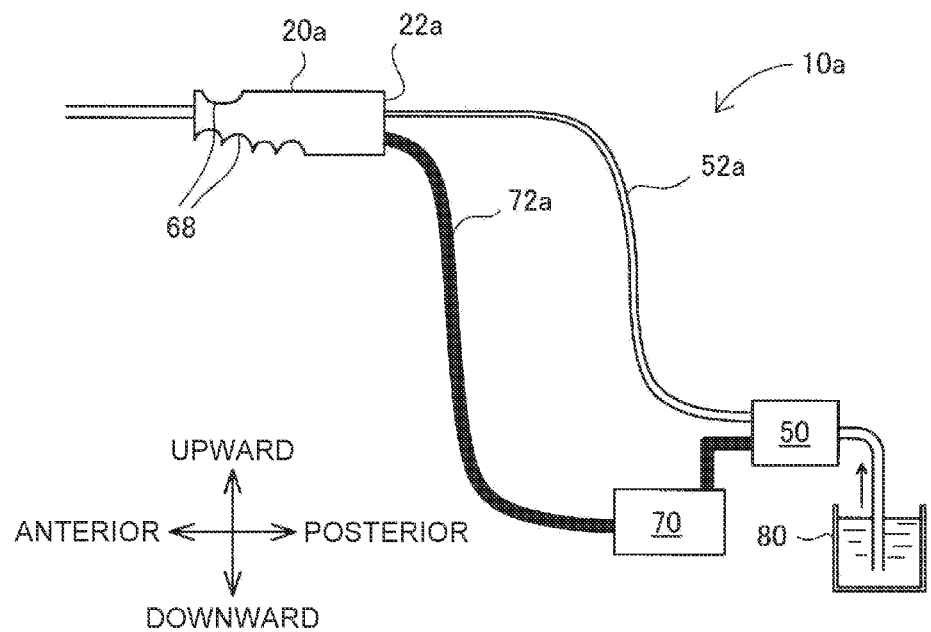
FIG. 7 is an explanatory diagram showing a hand piece with a grip.

In the embodiment, the suction force adjustment mechanism 65 is employed as the vertical orientation specification part, however, various configurations may be employed not limited to that. FIG. 7 is an explanatory diagram showing a hand piece 20a having a grip 68 as the vertical orientation specification part. The hand piece 20a specifies the vertical orientation by the shape of the grip 68. Further, FIG. 7 shows a liquid injection device 10a without the suction unit 60 or the suction channel 62. As described above, even in the case where the hand piece 20a does not include the suction force adjustment mechanism 65, the grip 68 is provided as the vertical orientation specification part, and thereby, the same advantages as those of the embodiment may be obtained.

Figure 8:
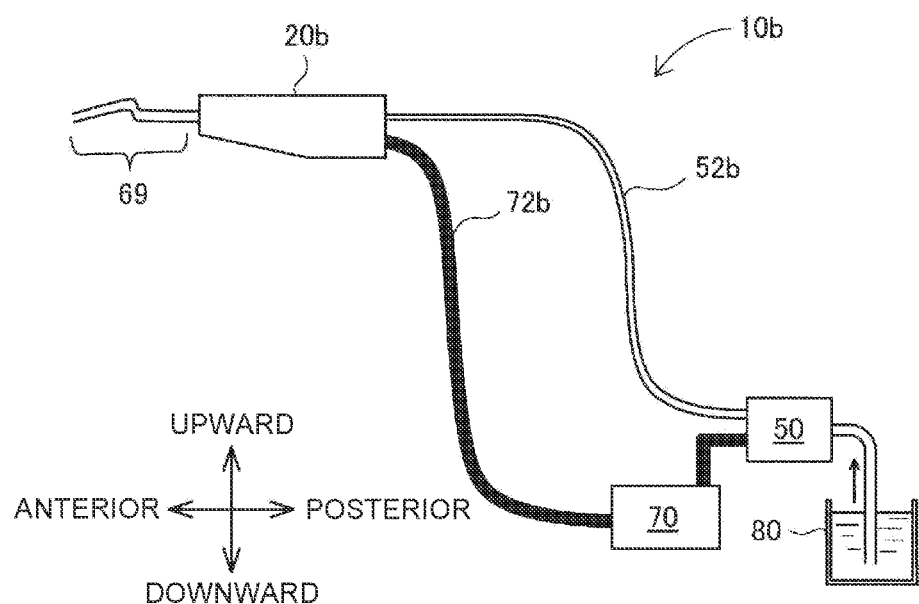
FIG. 8 is an explanatory diagram showing a hand piece with a curved portion on an injection tube.

FIG. 8 is an explanatory diagram showing a hand piece 20b having a curved portion 69 formed on an injection tube 55b as the vertical orientation specification part. The liquid injection device 10b specifies the vertical orientation of the hand piece 20b by the shape of the curved portion 69.

In addition, the vertical orientation may be specified using a line drawing such as an arrow or a character indicating the vertical orientation of the hand piece. The shape of the hand piece 20 may be a columnar shape having an oval section and the injection tube 55 may be drawn from above the center of the oval in the anterior end part 24 of the hand piece 20 for specification of the vertical orientation of the hand piece 20. The user may be informed of a predetermined vertical orientation by providing a tilt sensor or a level in the hand piece 20. The orientation of the hand piece 20 may be read by a sensor provided outside the hand piece 20 and the user may be informed of the vertical orientation.

The vertical orientation specification part may specify the vertical orientation of the hand piece as a function of the hand piece itself, may specify the vertical orientation of the hand piece as a function of a unit provided separately from the hand piece and contained in the liquid injection device, or may specify the vertical orientation of the liquid injection device in cooperation with another device than the liquid injection device 10.

The suction force adjustment mechanism 65 in the first embodiment specifies the vertical orientation of the hand piece 20 as an orientation in which the operability of the user and the function of the suction force adjustment mechanism 65 are preferably exhibited. The grip 68 shown in FIG. 7 specifies the vertical orientation of the hand piece 20 by the tactile sense of the user. A curved portion 69 shown in FIG. 8 specifies the vertical orientation of the hand piece 20 by the visual sense of the user. As described above, in the vertical orientation specification part, the vertical orientation may be specified as a use orientation of the hand piece 20 when the user uses the hand piece 20 or, when the function and the characteristic of the hand piece 20 change depending on the orientation of the hand piece 20, the vertical orientation of the hand piece 20 may be specified with reference to an orientation of the hand piece 20 in which the function and the characteristic are preferably exhibited. The vertical orientation specification part includes a part that provides information that specifies the vertical orientation of the hand piece 20 to the user via at least one of five senses of the visual sense, the tactile sense, the auditory sense, etc. of the user of the liquid injection device. The vertical orientation specification part includes a part that induces the user to sense the vertical orientation of the hand piece 20 for use from various elements of the shape, pattern, color, line drawing, character, mark, sound, light, operability, design, etc. of the configurations of the liquid injection device. Further, the vertical orientation specification part may suppress the use in other orientations than the vertical orientation specified by the user in advance depending on various elements of the liquid injection device.

(B6) Modified Example 6

In the embodiment, the liquid injection device 10 is used as a medical device. Note that the liquid injection device 10 may be used as another device than the medical device. For example, the liquid injection device 10 may be used as a cleansing device that removes dirt of a subject by applying the injected liquid to the subject, or a drawing device that draws characters, drawings, etc. with the injected liquid. According to the configurations, the same advantages as those of the embodiment may be obtained.

(B7) Modified Example 7

In the embodiment, the saline is employed as the liquid, however, various liquids including sterile water and pure water may be employed not limited to that.

(B8) Modified Example 8

In the embodiment, the second channel 41 and the connecting tube 54 may be formed by one member or may be formed by a plurality of members and a plurality of channels. Further, the curved shape may be formed by a combination of a plurality of members and a plurality of channels. Furthermore, part of the first channel 40 and the liquid feed channel 52 may be formed by one member or may be formed by a plurality of members.

(B9) Modified Example 9

In the embodiment, the posterior end surface 32a of the second case 32 is employed as the first surface, however, another surface of the actuator 30 may be employed as the first surface. The posterior end surface is preferable as the first surface.

What is claimed is:

1. A liquid injection device that injects a liquid comprising:
   a liquid chamber;
   a first channel connected to the liquid chamber and feeding a liquid to the liquid chamber;
   a second channel connected to the liquid chamber, to which the liquid is fed from the liquid chamber; and
   an injection tube that communicates with the second channel and injects the liquid,
   wherein the second channel has a curved shape, and
   wherein the first channel and the second channel each extend from a posterior surface of a second case the second channel extending anteriorly to the anterior surface of the second case, the liquid chamber being formed between a diaphragm and the second case, the second channel bending so as to extend toward an anterior surface of the second case.

2. The liquid injection device according to claim 1, wherein the first channel and the second channel are connected to a first surface of the liquid chamber, and the second channel is connected to a position different from a face center in the first surface.

3. The liquid injection device according to claim 2, wherein a curve angle X of the curved shape in the second channel is 90°≤X≤270°.

4. The liquid injection device according to claim 3, wherein the curve angle X is 180°±5°.

5. A medical device coupled to and using the liquid injection device according to claim 4.

6. A medical device coupled to and using the liquid injection device according to claim 3.

7. The liquid injection device according to claim 2, further comprising a vertical orientation specification part that specifies a vertical orientation of a container,
   wherein the second channel is connected to a more upper position of the first surface than the first channel in the vertical orientation specified by the vertical orientation specification part.

8. A medical device coupled to and using the liquid injection device according to claim 7.

9. A medical device coupled to and using the liquid injection device according to claim 2.

10. The liquid injection device according to claim 1, wherein the first channel and the second channel are connected to a first surface of the liquid chamber, and
    the first channel is connected to a position different from a face center in the first surface.

11. A medical device coupled to and using the liquid injection device according to claim 10.

12. The liquid injection device according to claim 1, wherein a section area of the second channel is five times or more larger than a section area of the first channel.

13. A medical device coupled to and using the liquid injection device according to claim 12.

14. The liquid injection device according to claim 1, wherein the second channel is formed by a metal member.

15. A medical device coupled to and using the liquid injection device according to claim 14.

16. A medical device using the liquid injection device according to claim 1.

* * * * *